United States Patent [19]

Rae et al.

[11] Patent Number: 5,116,856

[45] Date of Patent: May 26, 1992

[54] AMINOETHYLTHIAZOLE AND AMINOETHYLOXAZOLE DERIVATIVES

[75] Inventors: Duncan R. Rae, Lanark; Samuel G. Gibson, Motherwell, both of Scotland

[73] Assignee: Akzo N.V., Arnhem, Netherlands

[21] Appl. No.: 483,156

[22] Filed: Feb. 22, 1990

[30] Foreign Application Priority Data

Mar. 3, 1989 [EP] European Pat. Off. ........ 89302131.1

[51] Int. Cl.$^5$ .................. C07D 277/42; A61K 31/42
[52] U.S. Cl. .................. 514/370; 514/342; 546/280; 548/198; 548/233
[58] Field of Search .......... 548/198; 546/280; 514/370, 342

[56] References Cited

U.S. PATENT DOCUMENTS 2,636,037  4/1953  Sprague et al. ............. 548/194
4,018,786  4/1977  Amselem ..................... 548/194

OTHER PUBLICATIONS

G. Ferrand et al., "Syntheses de Derives Aminothiazoliques", Eur. J. of Med. Chem. Chim. Therapeutica, vol. 11, No. 1, Jan./Feb. 1976, pp. 49–55, France.

G. Ferrand et al., "Synthese et Proprietes Pharmacologiques de Derives Aminothiazoliques", Eur. J. of Med. Chem. Chim. Ther., vol. 10, No. 6, Nov./Dec. 1975, pp. 549–556, France.

C. Djerassi et al., "2-Substituted-4-(2-Dialkylaminoethyl) Thiazoles", J. of Org. Chem., vol. 15, No. 3, May 1950, pp. 700–706, US.

Primary Examiner—Robert Gerstl
Attorney, Agent, or Firm—Donna Bobrowicz; William M. Blackstone

[57] ABSTRACT

The invention relates to aminoethylthiazole and aminoethyloxazole derivatives with the general formula I

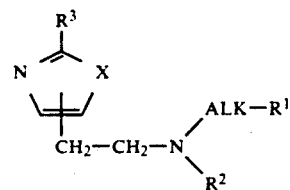

wherein
X is O or S;
ALK is a hydrocarbyl ($C_2$-$C_6$) group;
$R^1$ is a substituted or unsubstituted aryl group;
$R^2$ is a hydrogen, a hydrocarbyl ($C_1$-$C_6$) group or an aralkyl ($C_7$-$C_{13}$) group;
$R^3$ is a substituted or unsubstituted amino group;

or their pharmaceutically acceptable acid addition salts.

These new compounds are dopamine agonists with selectively for pre-synaptic dopamine receptors and, as such, are useful as anti-psychotics in the treatment of schizophrenia. The compounds are also useful in the treatment of hypertension, Parkinsonism and for the conditions of hyperprolactineamia, e.g. galactorrhea, menstrual disorders and amenorrhea.

4 Claims, No Drawings

AMINOETHYLTHIAZOLE AND AMINOETHYLOXAZOLE DERIVATIVES

The invention relates to aminoethylthiazole and aminoethyloxazole derivatives with the general formula I

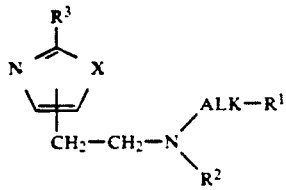

wherein
X is O or S;
ALK is a hydrocarbyl ($C_2$-$C_6$) group;
$R^1$ is a substituted or unsubstituted aryl group;
$R^2$ is a hydrogen, a hydrocarbyl ($C_1$-$C_6$) group or an aralkyl ($C_7$-$C_{13}$) group;
$R^3$ is a substituted or unsubstituted amino group;
or their pharmaceutically acceptable acid addition salts.

These new compounds are dopamine agonists with selectivity for pre-synaptic dopamine receptors and, as such, are useful--as anti-psychotics in the treatment of schizophrenia. The compounds are also useful in the treatment of hypertension, Parkinsonism and for the conditions of hyperprolactineamia, e.g. galactorrhea, menstrual disorders and amenorrhea.

Preferred compounds are compouds of formula I wherein X is S and ALK is an ethylene group. The most preferred compounds are those represented by formula II:

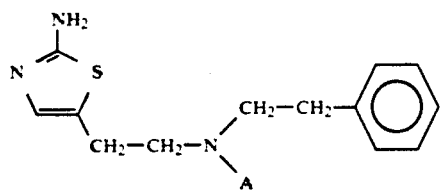

in which A is methyl, ethyl, propyl or allyl or their pharmaceutically acceptable acid addition salts.

The term hydrocarbyl ($C_2$-$C_6$) group, used in the definition of ALK, means an unbranched or branched, saturated or unsaturated hydrocarbon or cyclo-hydrocarbon with 2 to 6 carbon atoms, and more preferably with 2 to 4 carbon atoms. The most preferred is the ethylene group.

The term hydrocarbyl ($C_1$-$C_6$) group has the same meaning, but also includes the methyl group. Most preferred are the hydrocarbyl groups with 1 to 4 carbon atoms, such as methyl, ethyl, propyl, isopropyl, butyl and the like.

The term substituted or unsubstituted aryl group in the definition of $R^1$ means an aromatic group such as phenyl, naphthyl, pyridyl, thienyl, furanyl and the like, which optionally may be substituted with OH, halogen, $CF_3$, CN, $NO_2$, hydrocarbyl ($C_1$-$C_6$) or alkoxy ($C_1$-$C_6$).

The term alkoxy ($C_1$-$C_6$) in this definition means an alkoxy group, the alkyl constituent of which is defined as an alkyl group with 1 to 6 carbon atoms, such as methyl, ethyl, isobutyl, hexyl and the like. The preferred alkyl groups have 1 to 4 carbon atoms.

The term aralkyl ($C_7$-$C_{13}$) group means an aralkyl group with 7 to 13 carbon atoms, in which the aryl and alkyl groups have the previously given meanings.

The term substituted amino group means an hydrocarbyloxycarbonylamino ($C_2$-$C_7$) group or an amino group substituted by alkyl with 1 to 6 carbon atoms, as defined before, acyl ($C_1$-$C_{13}$) or aralkyl ($C_7$-$C_{13}$).

The term hydrocarbyloxycarbonylamino ($C_2$-$C_7$) group means a carbamate group derived from carbamic acid esterified with a hydrocarbyl alcohol, in which the hydrocarbyl group has 1 to 6 carbon atoms as defined before.

The term acyl ($C_1$-$C_{13}$) means an acyl group derived from an aliphatic or araliphatic carboxylic acid with 1-13 carbon atoms, such as formic acid, acetic acid, propionic acid, phenylacetic acid, cinnamic acid and the like. Preferred carboxylic acids are the lower aliphatic acids with 1 to 4 carbon atoms and the lower araliphatic carboxylic acids with 7 to 10 carbon atoms.

The compounds according to this invention are usually obtained as pharmaceutically acceptable acid addition salts, which are derived from suitable acids, such as hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid, methanesulphonic acid, and the like. Acid addition salts may be obtained by reaction of the free base according to formula I with an appropriate acid in a suitable solvent.

The compounds of this invention may be prepared by any method known for the preparation of analogous compounds.

Convenient starting products for the synthesis of compounds according to formula I are derivatives with the general formula III:

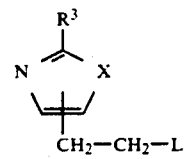

wherein X and $R^3$ have the previously given meanings and L is a leaving group such as a halogen atom or a sulphonyl group like the tosyl or mesyl group.

Compounds of formula III may be prepared by well-known methods, e.g. by reduction and halogenation or sulphonylation of derivatives of thiazole and oxazole substituted acetic acid, which may be obtained by methods known per se, e.g. as described in Chem. Abstracts, 74, 75415a or Beilsteins Handbuch der Organischen Chemie, vol 27, p. 336.

Compounds of formula III are condensed with an amine of formula IV:

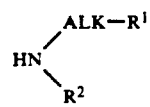

wherein ALK, $R^1$ and $R^2$ have the aforesaid meanings.

Compounds of formula I with a 2,5-di-substituted thiazole moiety may also be prepared from a heterocyclic compound with formula V

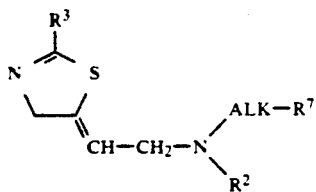

wherein $R^1$, $R^2$, $R^3$ and ALK have the previously given meanings.

Compounds of formula V are isomerized by acid treatment, e.g. by heating with hydrobromic acid to give above-mentioned compounds of formula I.

Compounds of formula V are prepared by methods known per se, e.g. by cyclizing thiourea derivatives.

Compounds of formula I may also be prepared from compounds with formula VI

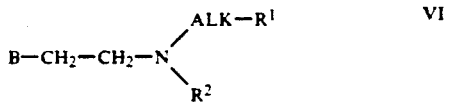

wherein ALK, $R^1$, and $R^2$ have the previously given meanings and B represents $CH_3$—CO— or CHO—$CH_2$—, by α—keto halogenation and reaction with a thiourea derivative with formula VII

wherein $R^3$ has the aforesaid meaning.

Still another general method for the synthesis of compound of formula I, is the reduction of an amide of formula VIII

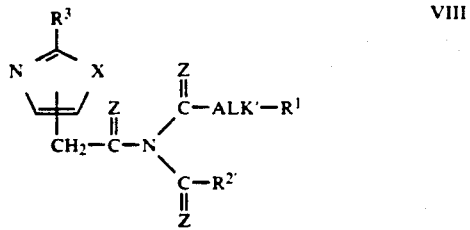

wherein X, $R^1$ and $R^3$ have the previously given meanings, C=Z is $CH_2$ or C=O with the proviso that at least one C=Z represents C=O,

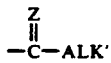

has the same carbon skeleton as ALK (as defined before) and

has the same carbon skeleton and substitution pattern as $R^2$ (as defined before).

The reduction may be performed by applying methods commonly used in the reduction of amides, e.g. by metalhydrides, and preferably $LiAlH_4$ on its own or mixed with $AlCl_3$ or borane in a suitable solvent, like tetrahydrofuran, diethylether, toluene and the like.

Compounds of formula I wherein $R^3$ is an amino group can be converted into substituted amino derivatives according to the general formula I by using known methods, e.g. reaction with alkyl-, aryl- or aralkylhalides, hydrocarbylchloroformate, carboxylic acid or by reductive alkylation.

Compounds according to this invention can be administered either enterally, locally or parenterally, in a daily dose between 0.01 and 50 mg/kg body weight, and preferably between 0.1 and 10 mg/kg body weight. For human use a daily dose between 5 and 500 mg is preferred. For this purpose the compounds are mixed with a suitable pharmaceutically acceptable carrier and processed in a form suitable for enteral, local or parenteral administration, for example a tablet, pill capsule, suppository, solution, emulsion, paste or spray. The oral form is the most preferred form of administration. The following examples further illustrate the preparation of the compounds used in this invention.

EXAMPLE 1 a) To a stirred solution of dicyclohexylcarbodiimide (1.07 g) in dry ether (14 ml) and carbon disulphide (6 ml) at −10° C., was added a solution of N-phenylethyl-N-propyl-2-butyne-1,4-diamine (1.2 g) in dry ether (3.2 ml). After 0.5 hours the temperature was raised to +20° C. for a further 1.5 hours, and the resultant solid was filtered off. The filtrate was evaporated under reduced pressure to give a gum (1.58 g) which was redissolved in dry ether (5 ml). This solution was added to a stirred saturated solution of ammonia in dry ether (19 ml) at 0° C. while bubbling a slow stream of ammonia into the reaction. After 3 hours the solvent was evaporated under reduced pressure to leave N-phenylethyl-N-propyl-N'-thioamido-2-butyne-1,4-diamine (1.65 g) as an oily-gum.

b) A slow stream of hydrogen chloride was bubbled into a stirred solution of N-phenylethyl-N-propyl-N'-thioamido-2-butyne-1,4-diamine (1.65 g) in ethanol (10 ml) at 0° C. for 20 minutes. Ater 45 minutes the solvent was evaporated under reduced pressure to give an oil which was partially dissolved in water and the nonbasic impurities were extracted with dichloromethane (3×50 ml). An excess of 4N sodium hydroxide solution was added to the aq. phase and the product was extracted with dichloromethane (3×50 ml). The extracts were washed with dilute aq. sodium chloride solution to leave 5-[2-(phenylethylpropylaminoethylidine)]-4[H]-thiazol-2-amine (1.30 g) as an oil, which crystallized on ageing.

c) A stirred solution of 5-[2-(phenylethyl-propylamino-ethylidine)]-4[H]-thiazol-2-amine (43.3 g) in 48% hydrobromic acid (430 ml) was heated at 120° C. for 40 mins. The reaction solution was poured into ice (430 g) and 10N potassium hydroxide solution (430 ml) was added. The basified material was extracted with dichloromethane (3 ×100 ml), the extracts were washed with dilute aq. sodium chloride solution (2×100 ml), dried ($Na_2SO_4$) and evaporated under reduced pressure to leave an oil (43 g), which was purified by chromatography to give 32 g of pure material.

A solution of (E)-2-butenedioic acid (12.84 g) in methanol was added to a solution of this free base (32.0 g) in methanol yielding 5-[2-(phenylethylpropylaminoethyl)]-thiazol-2-amine (E),-2-butenedioate 1:1 salt in 2 crops (36.3 g) which was recrystallized from methanol/ether and dried in vacuo at 70° C. for 5 hours. Yield 30.0 g, m.p. 146°-147.5° C..

EXAMPLE 2

In an analogous manner as described in Example 1, were prepared:
5-[2-(propyl-2-thienylethylaminoethyl)]-thiazol-2-amine (E)-2-butenedioate 1:1 salt, m.p. 130°-133.5° C.;
5-[2-(ethylphenylethylaminoethyl)]-thiazol-2-amine (E)-2-butenedioate 1:1 salt, m.p. 121°-127° C.;
5-[2-methylphenylethylaminoethyl)]-thiazol-2-amine (E)-2-butenedioate 2:3 salt, m.p. 141°-145° C.; 5-[2-(phenylethyl-2-propenylaminoethyl)]-thiazol-2-amine (E)-2-butenedioate 1:1 salt, m.p. 120°-123° C.;

EXAMPLE 3

A stirred mixture of 5-(2-(chloroethyl)-thiazol-2-amine (2.40 g), N-propyl-benzeneethanamine (2.90 g) and anhydrous potassium carbonate (2.04 g) was heated at 125° C. for 4 hours. Dichloromethane (15 ml) was added, the inorganic salts removed by filtration and the filtrate evaporated under reduced pressure to leave a dark gum (5.45 g), which was purified by chromatography to give 2.12 g of pure material.

A solution of (E)-2-butenedioic acid (0.77 g) in methanol was added to a solution of the free base (1.92 g) in methanol, yielding the salt (2.09 g) which was recrystallized from methanol/ether and dried to give 1.81 g of the product described in example 1 (c).

EXAMPLE 4

In an analogous manner as described in Example 3 was prepared:
5-[2-(phenylethylpropylaminoethyl)]-oxazol-2-amine (E)-2-butenedioate 1:1 salt.

EXAMPLE 5

Thiourea (1.99 g) was added to a stirred solution of 1-bromo-4-(phenylethylpropylamino)-2-butanone (10.27 g) in 1:1 aqueous ethanol (88 ml) and the solution was allowed to stand at room temperature for 20 hrs. The reaction was basified with 33% ammonia and the product extracted into ether (3×100 ml). The combined ether extracts were dried over $Na_2SO_4$ and evaporated under reduced pressure to leave a gum (6.45 g) which was purified by chromatography to give 3.33 g of pure material.

A solution of (E)-2-butenedioic acid (1.33 g) in methanol was added to a solution of the free base (3.33 g) in methanol and on addition of dry ether the product crystallized out to give 4-[2-(phenyl-ethylpropylaminoethyl)]-thiazol-2-amine(E)-2-butenedioate 1:1 salt (2.45 g). This was dried in vacuo at 70° C. for 8 hrs. m.p. 119°-122° C.

EXAMPLE 6

A solution of 5-[2-(phenylethylpropylaminoethyl)]-thiazol-2-amine (1.4 g) in formic acid (2.8 ml) and formamide (5.6 ml) was heated on a steam bath for 5 hrs, then poured into water and basified with aqueous ammonia. The product was extracted with ether, the extract was washed with water, dried ($Na_2SO_4$) and evaporated to give 1.5 g of a colourless oil which was purified by chromatography (silica). The purified material (1.05 g) was treated with fumaric acid to give N-formyl-5-[2-(phenylethylpropylaminoethyl)]-thiazol-2-amine(E)-2-butenedioate 2:1 salt (0.93 g), m.p. 138-143° C.

EXAMPLE 7

To a solution of 5-[2-(phenylethylpropylaminoethyl)]-thiazol-2-amine (1.4 g) and sodium bicarbonate (1.5 g) in methylene chloride (30 ml) was added vinyl chloroformate (0.65 ml) in a rapid dropwise manner and the reaction was boiled under reflux for 20 min.

Water was added and after stirring for 15 mins the organic layer was separated, washed with water, dried ($Na_2SO_4$) and evaporated to give 1.67 g of gum, which was converted to ethenyl 5-[2-(phenylethylpropylaminoethyl)]-thiazol-2-carbamate(E)-2-butenedioate 1:1 salt (1.45 g), m.p. 125-136° C., in the usual manner.

EXAMPLE 8

In an analogous manner as described in Example 7 was prepared ethenyl 5-[2-(ethylphenylethylaminoethyl)]thiazol-2-carbamate(E)-2-butenedioate 1:1 salt, m.p. 139° C..

We claim:

1. Aminoethylthiazole and aminoethyloxazole derivatives with the general formula I

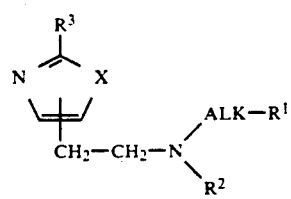

wherein
X is S;
ALK is a hydrocarbyl ($C_2$-$C_6$) group and selected from the group consisting of unbranched hydrocarbons, branched hydrocarbons, saturated hydrocarbons, unsaturated hydrocarbons, and cyclohydrocarbons of 2 to 6 carbon atoms;
$R^1$ is a substituted or unsubstituted aryl group selected from the group consisting of phenyl, naphthyl, pyridyl, thienyl, and furanyl, any member of said aryl group may be substituted with a substituent selected from the group consisting of OH, halogen, $CF_3$, CN, $NO_2$, hydrocarbyl containing from 1 to 6 carbon atoms and alkoxy containing from 1 to 6 carbon atoms;
$R^2$ is a hydrogen, a hydrocarbyl group containing from 1 to 6 carbon atoms and selected from the group consisting of methyl, unbranched hydrocarbons, branched hydrocarbons, saturated hydrocarbons, unsaturated hydrocarbons, and cyclohydrocarbons of 2 to 6 carbon atoms or an aralkyl group containing from 7 to 13 carbon atoms wherein aryl is defined in $R^1$ and alkyl is defined as ALK; and
$R^3$ is a substituted or unsubstituted amino group wherein the substituted amino group is selected from the group consisting of a hydrocarbyloxycarbonylamino comprising 2 to 7 carbon atoms, an amino group substituted by alkyl with 1 to 6 carbon atoms, an amino group substituted by acyl comprising 1-13 carbon atoms derived from a aliphatic or araliphatic carboxylic acid with 1 to 13 carbon atoms and an amino group substituted by aralkyl containing 7-13 carbon atoms;

or the pharmaceutically acceptable acid solution salts thereof.

2. Compounds according to claim 1, wherein X is S ALK is an ethylene group.

3. Compounds according to claim 1, with the formula II:

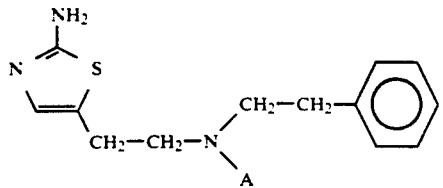

in which A is methyl, ethyl, propyl or allyl or the pharmaceutically acceptable acid addition salts thereof.

4. Pharmaceutical composition comprising a compound according to claim 1 in an effective amount for treating diseases amenable to treatment with dopamine agonists in admixture with a pharmaceutically acceptable carrier.

* * * * *